United States Patent
Juarez et al.

(10) Patent No.: US 9,932,647 B2
(45) Date of Patent: *Apr. 3, 2018

(54) ***GLOMUS IRANICUM* VAR. *TENUIHYPHARUM* VAR. NOV. STRAIN AND USE THEREOF AS BIO-NEMATICIDE**

(71) Applicant: SYMBORG, S.L., Murcia (ES)

(72) Inventors: Jesus Juarez, Murcia (ES); Felix Fernandez, Murcia (ES)

(73) Assignee: SYMBORG, S.L., Murcia (ES)

(*) Notice: Subject to any disclaimer, the term of this patent is extended or adjusted under 35 U.S.C. 154(b) by 118 days.

This patent is subject to a terminal disclaimer.

(21) Appl. No.: 15/034,078

(22) PCT Filed: Apr. 8, 2014

(86) PCT No.: PCT/EP2014/057067
§ 371 (c)(1),
(2) Date: May 3, 2016

(87) PCT Pub. No.: WO2015/000613
PCT Pub. Date: Jan. 8, 2015

(65) Prior Publication Data
US 2016/0319380 A1    Nov. 3, 2016

(30) Foreign Application Priority Data
Jul. 2, 2013 (EP) .................................... 13174717

(51) Int. Cl.
*A01N 63/00* (2006.01)
*C12R 1/645* (2006.01)
*A01N 63/04* (2006.01)
*C12N 1/14* (2006.01)
*A01H 17/00* (2006.01)

(52) U.S. Cl.
CPC ............. *C12R 1/645* (2013.01); *A01H 17/00* (2013.01); *A01N 63/04* (2013.01); *C12N 1/14* (2013.01)

(58) Field of Classification Search
CPC .................................................... C12R 1/645
See application file for complete search history.

(56) References Cited

PUBLICATIONS

S. Appoloni, et al; Molecular community analysis of arbuscular mycorrhizal fungi in roots . . . ; Microb. Ecol.; 2008; vol. 56; pp. 649-659.
International Search Report dated Jul. 11, 2014 for PCT/EP2014/057067.

*Primary Examiner* — Albert M Navarro
(74) *Attorney, Agent, or Firm* — Lucas & Mercanti, LLP (57) ABSTRACT

*Glomus iranicum* var. *tenuihypharum* var. nov. strain deposited under BCCM deposit number 54871, comprising the sequence identified by SEQ ID NO: 1; composition comprising said strain, 2:1 smectite clays, metal ions and chitin and use thereof as bio-nematicide. The invention also discloses a composition comprising said strain, fungicides, bio-fungicides, insecticides, bio-insecticides, nematicides and bio-nematicides.

19 Claims, 2 Drawing Sheets

SEQUENCE LISTING

```
<160> NUMBER OF SEQ ID NOS: 1

<210> SEQ ID NO 1
<211> LENGTH: 813
<212> TYPE: DNA
<213> ORGANISM: Glomus iranicum var. tenuihypharum var. nov.
<220> FEATURE:
<221> NAME/KEY: source
<222> LOCATION: 1..813
<223> OTHER INFORMATION: /mol_type="unassigned DNA"
      /note="18S (partial sequence)-ITS1 (complete sequence)-5.8S
      (partial sequence)"
      /organism="Glomus iranicum var. tenuihypharum var. nov."

<400> SEQUENCE: 1
cctgcggctt atttgactca acacggggaa actcaccagg tccagacata gtaaggattg      60
acagattgag agctctttct tgattctatg ggtggtggtg catggccgtt cttagttggt     120
ggagtgattt gtctggttaa ttccgttaac gaacgagacc ttaacctgct aaatagctag     180
gcttaacttc ggttaggtcg tcagcttctt agagggacta tcggtgttta accgatggaa     240
gtttgaggca ataacaggtc tgtgatgccc ttagatgttc tgggccgcac gcgcgctaca     300
ctgatgaagt catcgagttc atttccttta tcggaagata tgggtaatct tttgaaactt     360
catcgtgctg gggatagagc tttgcaatta ttgctcttaa acgaggaatc cctagtaagc     420
acaagtcatc agcttgtgct gattacgtcc ctgcccttg tacacaccgc ccgtcgctac     480
taccgattga atggcttagt gaggccctcg gatcgacgct cggagactgg caacagtttc     540
cgttcgttga gaagttggtc aaacttggtc atttagagga agtaaaagtc gtaacaaggt     600
ttccgtaggt gaacctgcgg aaggatcatt attgatttag cgaaccgagc gttagcgagg     660
ttctgcgatc gcttatattt aaaacccact cttaacgtat aaaattttta ttaatgatga     720
aaaaaaatag atcactctat aaaatcggaa aacccgctta aattttttta tgtctttcga     780
atagataaaa aaaaatatca ctttcaacaa cgg                                  813
```

GLOMUS IRANICUM VAR. TENUIHYPHARUM VAR. NOV. STRAIN AND USE THEREOF AS BIO-NEMATICIDE

CROSS REFERENCE TO RELATED APPLICATION

This Application is a 371 of PCT/EP2014/057067 filed on Apr. 8, 2014, which, in turn, claimed the priority of European Patent Application No. 13174717.2 filed on Jul. 2, 2013, both applications are incorporated herein by reference.

FIELD OF THE INVENTION

The invention relates to the agronomic field. Specifically, the present invention relates to a composition comprising a *Glomus iranicum* var. *tenuihypharum* var. nov. strain and other components, which is used as bio-nematicide.

BACKGROUND OF THE INVENTION

Mycorrhizal compositions made so far have a natural limit of mycorrhizal propagules. Said limit is mainly due to the strain used and the method for obtaining the mycorrhizal compositions.

Phytoparasitic nematodes are a global threat to agricultural production. There are over 40 genera that act as obligate parasites of higher plants. One of the methods available for crop protection is the use of synthetic chemicals, but many of these products have adverse effects on humans and can be toxic to the environment. Alternatively, farmers may choose to use biological approaches as mycorrhizal fungi that colonize the roots of crop plants and reduce nematode damage thanks to compensation and increased root system and increased nutrient absorption. However, mycorrhiza-forming fungi presently available do not produce mycelium consistently, do not achieve a high degree of mycorrhizal colonization and do not achieve high effectiveness in intensive agriculture crops. The invention described herein provides a new strain of mycorrhiza-forming fungus showing improved performance over other fungi and products described in the state of the art.

DESCRIPTION OF THE INVENTION

One embodiment of the invention is a strain of *Glomus iranicum* var. *tenuihypharum* var. nov. deposited under BCCM deposit number 54871, comprising the sequence identified by SEQ ID NO: 1.

The *Glomus iranicum* var. *tenuihypharum* var. nov. strain of the invention, isolated from a Solonetz Gley saline sodic soil in the town of Fortuna, Murcia (Spain), was deposited on 19 Apr. 2013 at the international depositary authority Belgian Coordinated Collections of Micro-Organisms (BCCM) with the address at Université Catholique de Louvain, Mycothèque de l'Université catholique de Louvain (MUCL), Croix du Sud 2, Box L7.05.06, 1348 Louvain-la-Neuve, by Symborg, S. L., with address at Ceeim Building, University Campus, S/N, 30100 Murcia, Spain.

The *Glomus iranicum* var. *tenuihypharum* var. nov. strain has been identified by the depositor by the reference SYMBORG-001, and received the deposit number 54871 by the international depositary authority.

The sporocarps of the *Glomus iranicum* var. *tenuihypharum* var. nov. strain of the invention are unknown. Said strain spores occur singly or in loose clusters in the soil and they can also be formed sporadically in the roots. Spores are hyaline to ocher light, with subglobose to globular shape (rarely irregular), relatively small (24.0) 30.7±3.7 (42) microns in diameter, composed of two layers of wall (1-4 m thick) an interior laminated compact layer (0.5-1.5 m), and an outer semi-permanent layer, roughened in young spores and of somewhat rough appearance in adult spores and larger than 0.5 to 2.0 m thick. The walls of the interior spore of young spores have a reddish brown staining with Melzer's reagent, but the color disappears on the staining of mature spores, and the contents of the spores have a pale appearance. The hypha that holds the spore has a hyaline to pale ocher color, is straight or wavy of 2.5 to 4.5 micron in diameter (average of 3.0 micron), cylindrical and with a slight funnel shape which merges with the open-pored layers of the spore wall, at least in mature spores. Germination Structure: germ tube that grows and develops back through the union of the hypha with the spore. It forms vesicular arbuscular mycorrhizae.

The mycelium forms an extensive network. The extramatrical mycelium is hyaline to pale yellow, profuse and the spores appear always in the soil matrix, forming abundant sporocarps in group (2 to 8 individual spores). The unique feature of this species is the large amount of external mycelium network and the inability to grow under in vitro association of transformed roots.

The strain was isolated from a Solonetz Gley type saline soil. The main feature of these soils is that they are very hydromorphic, very compact and with a lot of salt deposits on the surface.

The strain was isolated from a soil located in the town of Fortuna, Murcia (Spain).

The following table shows some chemical properties of the original soil where the *Glomus iranicum* var. *tenuihypharum* var. nov. strain was isolated.

TABLE 1

Soil properties

| Parameters | Values |
| --- | --- |
| pH ($H_2O$) | 8.5 |
| $CaCO_3$ (%) | 12 |
| C/N | 6.5 |
| $Ca^{++}$ (ppm) | 5809.6 |
| $Mg^{++}$ (ppm) | 2,967.04 |
| $K^+$ (ppm) | 2955 |
| $Na^+$ (ppm) | 1829.4 |

According to a phylogeny based on 813 base pairs of the ribosomal RNA 18S (partial sequence), ITS1 (internal transcribed spacer 1, complete sequence) genes and the ribosomal RNA 5.8S (partial sequence) gene, the strain of the invention is categorized into a clade consisting of *Rhizophagus* (before *Glomus* Ab group, represented by *Rhizophagus irregularis, Glomus intraradices* and *Rhizophagus bistratum*).

According to this phylogeny *Glomus indicum* and *Glomus achrum* are the closest relatives. Around fifty sequences of uncultured *Glomus* spp. clones can be found with a high identity (99%) to the sequence of the strain of the invention in the NCBI server (gene bank).

It appears therefore that the new taxon has a cosmopolitan distribution and a wide host range. Very similar sequences have originated in Japan (Ogura-Tsujita Y. et al. 2013. Arbuscular mycorrhiza formation in cordate gametophytes of two ferns, *Angiopteris lygodiifolia* and *Osmunda japonica*. *Journal of Plant Research*. 126 (1): 41-50; Yamato M. et al. 2011. Arbuscular mycorrhizal fungi in roots of nonphotosynthetic plants, *Sciaphila japonica* and *Sciaphila tosaensis* (Triuridaceae). *Mycoscience* 52: 217-223.), New Zealand, Africa and North America (Appoloni S. et al. 2008. Molecular community analysis of arbuscular mycorrhizal fungi in roots of geothermal soils in Yellowstone National Park (USA). *Microbial Ecology* 56 (4): 649-659).

The most striking morphological character of the strain of the invention is the small size of the spores and the hyaline to very light ocher coloration and that they occur singly or in small groups on the soil.

The only strain of *Glomus* sp. with hyaline spores that are similar in size and color to the strain of the invention is *Glomus iranicum* (Blaszkowski J et al. (2010). *Glomus africanum* and *G. iranicum*, two new species of arbuscular mycorrhizal fungi (Glomeromycota). *Mycologia* 102: 1450-1462.) (Table 1). The three layers of the wall of the spores are morphologically indistinguishable from that of the strain of the invention. There is a clear difference in the strain of the invention and it is that the size of their hyphae attached to the spore is very fine.

The outer wall L1 of spores of *Glomus iranicum* (Blaszkowski J et al. (2010). *Glomus africanum* and *G. iranicum*, two new species of arbuscular mycorrhizal fungi (Glomeromycota). *Mycologia* 102: 1450-1462.) deteriorates rapidly and consistently, with strong dextrinoid activity, however in the case of the strain of the invention, it is only observed in very young spores, thus it is concluded that it is a variety of *Glomus iranicum* and we propose the new variety *tenuihypharum*.

This is a strain that adapts to and tolerates perfectly saline environments and fertilizer solutions with high electrical conductivities.

The species produces abundant extramatrical mycelium, which ensures proper symbiotic functioning.

The species reaches high concentrations of internal colonization in short periods of time, especially in crops under intensive agriculture, indicating a high effectiveness of performance under these conditions.

Due to the small size of their spores and abundant extramatrical mycelium, as well as the recovery capacity of the same due to physical damage, the strain can be handled and ground to below 80 microns, remaining totally viable on a clay substrate for more than two years and a proven effectiveness in a range of $1.2\times10^4$ to $1\times10^8$ infective propagules/100 ml$^{-1}$ of soil.

The application of this species promotes an effective response in productivity of crops under intensive agriculture, and keeps high levels of physiological activity at the expense of a low energy cost, given by the low rates of transpiration that promote high and efficient use of the water.

The strain promotes a radical change of the root architecture, promoting a different root system, horizontal and with greater dichotomy induced by quick internal and external mycorrhizal colonization, and the need for greater amount of host root cells, which also promote a greater development of roots in the short and long term.

Another important aspect to be assessed is the microbial activity generated by this organism in the rhizosphere system. This strain produces a constant stimulation of the rhizospheric microbiota in the treated plants. This fact is due to the own exudation of nutritional elements through the rootlets, mycorrhizae and hyphae stimulating both micorizosphere and rhizosphere activity in the vicinity of the external mycelium of the *Glomus iranicum* var. *tenuihypharum* var. nov. strain, which produces a higher microbial concentration at each of the moments tested.

*Glomus iranicum* var. *tenuihypharum* var. nov. is a species of excellent mycorrhiza-forming fungus.

Another embodiment is a composition comprising a strain of *Glomus iranicum* var. *tenuihypharum* var. nov. deposited under BCCM deposit number 54871 comprising the sequence identified by SEQ ID NO: 1, 2:1 smectite clays, metal ions and chitin.

In particular, said 2:1 smectite clays are dioctahedral or trioctahedral. And also in particular, said 2:1 smectite clays are selected from the group consisting of sepiolite, attapulgite, nontronite and saponite.

The present invention utilizes clay of the dioctahedral or trioctahedral smectite, sepiolite and attapulgite type, all with high plasticity when wetted and consisting of a very fine granular material, consisting of very small particles the size of which is less than 4 microns, and its main property is the expansion in systems with low water availability as it may be a substrate for mycorrhizal fungi reproduction. On the other hand, it is very important the colloid formation and disintegration in the presence of abundant water when applied in localized irrigation systems. These types of clays upon completion of one of the production phases of the inoculant, provide the mycorrhizal propagules with: spores, extramatrical mycelium and colonized rootlets; stressful situations that promote subsequent acceleration of the germination processes once inoculated under intensive and ecological crops conditions.

Another embodiment is the composition of the invention, wherein the concentration of said *Glomus iranicum* var. *tenuihypharum* var. nov. is between 0.05 and 4% by weight. In particular, the concentration is between 0.1 and 3% by weight.

Another embodiment is the composition of the invention wherein the chitin concentration is between 2 and 10% by weight.

Another embodiment is the composition of the invention, wherein said metal ions are selected from the group consisting of Fe, Ca and Mg.

In particular, the composition of the invention comprises Fe, Ca and Mg.

Another embodiment is the composition of the invention, wherein the concentration of Fe is between 3 and 12% by weight, the concentration of Ca is from 0.5 to 5% by weight and the concentration of Mg is from 0.2 to 2% by weight.

Due to its mycorrhizal expression, it is good to highlight the rich and significant production of extramatrical mycelium and of easily extractable Glomalin that occurs in the presence of the species *Glomus iranicum* var. *tenuihypharum* var. nov. regardless of the fertilization used, indicative of the adaptation of this microorganism to various saline environments.

The plants treated with *Glomus iranicum* var. *tenuihypharum* var. nov. exhibit increased production of leaf and root biomass, related in turn to a higher concentration of nutrients in leaves in the presence of the largest fertilizer dosages, indicative of the high tolerance to these conditions.

The application of *Glomus iranicum* var. *tenuihypharum* var. nov. produces high photosynthetic activity at the expense of lower rates of perspiration, which leads the treated plants to make a more efficient use of water throughout the crop, both at doses of 50% and of 100% of the fertilizer applied.

*Glomus iranicum* var. *tenuihypharum* var. nov. strain has high activity of the *Glomus iranicum* var. *tenuihypharum* var. nov. strain relative to the rest of inoculants used in Example 1, possibly derived from the nature of the species itself, highly symbiotic, superproducer of extramatrical mycelium, Glomalin and a strong interior colonization, which in turn produces an adequate physiological activity with low stomatal conductance, leading to an efficient use of water with high productivity, even with higher doses of fertilizer.

Another embodiment is the composition of the invention, wherein the form of presentation of said composition is powder, emulsifiable concentrate or granules.

Another embodiment is the composition of the invention, wherein said composition is a liquid, a solid or a gel.

Another embodiment is the composition of the invention comprising at least one fungicide, at least one bio-fungicide, at least one insecticide, at least one bio-insecticide, at least one nematicide and/or at least one bio-nematicide.

In particular, said fungicide is selected from the group consisting of Maneb, Mancozeb, Metalaxyl-Ridomil, Myclobutanil, Olpisan, Propamocarb, Quintozene, Streptomycin, Sulfur, Thiophanate-methyl, Thiram, triforine, vinclozolin, Zinc white, Zineb, Ziram, Banrot, Fixed copper, Chlorothalonil, Chlorothalonil, Captan, Chloroneb, Cyproconazole, Zinc ethelene, bisdithiocarbamate, Etridiazole, Fenaminosulf, Fenarimol, Flutolanil, Folpet, Fosetyl-AL and Iprodione.

In particular, said bio-fungicide is selected from the group consisting of *Trichodermas* sp, *Bacillus subtilis, Bacillus licheniformis, Bacillus pumilus, Bacillus amyloliquefaciens, Streptomyces* sp, *Coniothyrium minitans* and *Pythium oligandrum*.

In particular, said insecticide is selected from the group consisting of organophosphate, carbamate and neonicotinoid.

In particular, said bio-insecticide is selected from the group consisting of *Bacillus* sp., *Chromobacterium* sp., *Beauveria* sp. and *Metarhizium* sp.

In particular, said nematicide is organophosphate or carbamate.

In particular, said bio-nematicide is *Pasteuria* sp.

Another embodiment is the method for obtaining the composition of the invention, comprising:
(a) coating inoculation of a seed of a host plant with *Glomus iranicum* var. *tenuihypharum* var. nov. deposited under BCCM deposit number 54871,
(b) cultivating said plant in watering cycles of between 7 to 10 days on a reproduction substrate comprising smectite clays in a percentage above 52% of the total weight of said substrate,
(c) discontinuing said watering for a period equal to or greater than 20 days,
(d) removing the aerial part of the plant and removing the substrate and
(e) milling said substrate below 80 microns at a temperature between 25 and 30° C. to obtain said composition.

In Example 1, the composition of the invention has shown a high efficiency as bio-nematicide. It was found that the treatment with the composition of the invention showed a more vigorous initial development which was maintained throughout the growing cycle.

The most important fact is that all treatments experience a sharp productive decline from about day 140 from transplant, and the plants show severe decay with the natural aging and temperature rise characteristic of the dates, which favor the proliferation of nematode colonies. This results in the obtainment of very small fruits of no commercial value.

The second inoculation of the products with the composition of the invention and application of the product to be compared (Vydate), reactivates again the production and vegetative growth of the plants in a general way in all treatments, with the products *Glomus iranicum* var. *tenuihypharum* var. nov. and the composition of the invention showing a greater vigor and early recovery of the plant. This is due to the quick action of this species causing the acceleration of root activity in the plant, showing a better performance than the product to be compared and arriving with better appearance and performance at the end of the assay, both in the curative and in the preventive part. To avoid this sharp drop in production it is recommended to carry out the second inoculation of the composition of the invention at approximately 120 days to block the spread of the nematode and promote again root development.

Better performance was obtained in both tomato varieties of Example 2 with treatment with the composition of the invention reaching almost 13 kg/plant of Daniela variety, and 5 kg/plant Raf variety, with the fruits of this treatment being the largest, which shows a better uptake of water and nutrients in the fruit.

Another embodiment is the use of the composition of the invention as bio-nematicide, hereinafter use of the invention.

Another embodiment is the use of the invention, wherein the composition of the invention is applied to the plant by seed treatment, root treatment, roots embedded in an emulsion, addition to irrigation water, irrigation, application of powder to the root system or application of emulsion injected into the root system.

PREFERRED EMBODIMENTS

Example 1

Genetic Identification of the Strain of the Invention
DNA Extraction

Isolated hyphae and spores were transferred to 1.5 ml Eppendorf tubes with 0.2 g of glass beads (2 mm diameter) and 100 µL of CTAB buffer (2% CTAB=Cetyl trimethyl ammonium bromide, 1.4 M NaCl, 0.1 M Tris-HCl pH 7.5, 0.2 M Na-EDTA).

This mixture was homogenized using a ball mill type Retsch MM301 at full speed for 30 seconds. Additional 400 µL of CTAB buffer were added and the mixture was incubated at 65° C. for one hour. Subsequently 400 µL of Chloroformo-isoamyl alcohol (24:1) were added and mixed by inverting the reaction tubes and then it was centrifuged for 5 min at 10,000×g, and the upper layer was recovered in a clean Eppendorf tube. This step was repeated twice. 200

μL of 5 M ammonium acetate were added to this suspension, the mixture was incubated at 4° C. for 30 minutes, followed by 20 minutes of spinning at 4° C. and 13,000 rpm. The DNA was precipitated with 700 μL of isopropanol at −20° C. overnight. The DNA pellet obtained was precipitated with isopropanol and washed with 70% ice-cold ethanol, air dried and re-dissolved in 50 μL of Tris ethylene diamine buffer (10 mM Tris, 10 mM EDTA, pH 8)+4.5 U RNase/ml.

PCR Conditions

The primers used for PCR amplification and for sequencing the internal transcribed spacers region of the 18S rDNA gene were Glom1310 and ITS4i (Redecker, 2000). Amplifications were performed in 0.2 mM dNTP-mix, 1 mM of each primer, 10% of PCR reaction buffer and double distilled sterile water. GoTaq® DNA polymerase (Promega, Mannheim, Germany) was added to 3.75 u/100 μL of reaction mixture; 2 μL of genomic DNA template was used in each 20 μL/reaction. Amplifications were carried out in a advanced thermal cycler Primus 96—(peqLab Biotechnology) in 200 reaction tubes mu 1 (94° C., 120 s initial denaturation, followed by 30 cycles of 94° C. 15 s, 52° C., 30 s, 72° C., 45 s, and a final slope at 72° C. for 120 s).

Data Analysis

The alignment was carried out initially using the computer program BioEdit 7.0. Phylogenetic analyses by maximum likelihood (ML) were carried out with the PHYML program. The nucleotide substitution model GTR was used with ML estimates of the base frequencies. The proportion of invariable sites were estimated and optimized. Four categories of the substitution rate were developed and the gamma distribution parameter was also estimated and optimized. Bootstrap analysis was used with 100 replicates to test the statistical support of the branches.

Sequencing

Excess primers and dNTPs were removed by column chromatography (Microspin S-300 HR, Amersham Biosciences). For partial sequencing of the 18S-ITS1-5.8S region primers Glom1310 and ITS4i were used in a concentration of 1.6 mM. Sequencing was carried out with PRISM Big-Dye™ Terminator Cycle Sequencing Kit from ABI (Applied Biosystems) according to the manufacturer's recommendations. The parameters for sequencing were delay 18 seconds at 96° C., followed by 25 cycles with 18 sec at 96° C., 5 seconds at 50° C. and 4 min at 60° C. Sequence analysis was performed using an automated sequence analyzer (ABI PRISM 3130, Applied Biosystems) in conjunction with the ABI Prism™ Auto Assembler software (version 140, Applied Biosystems).

Ribosomal RNA 18S sequence (partial sequence), ITS1 (complete sequence) and ribosomal RNA 5.8S gene (partial sequence) were obtained from the strain of the invention, which sequence is identified by SEQ ID NO: 1.

Example 2

Effectiveness of the Composition of the Invention on Tomato Crop

The assay was divided into two parts, preventive treatment and curative treatment, divided into 5 treatments:
- $T_1$: Control Treatment
- $T_2$: Treatment with *Glomus iranicum* var. *tenuihypharum* var. nov mycorrhizal inoculum.
- $T_3$: Treatment with product to be tested. (Composition of the invention, *Glomus iranicum* var. *tenuihypharum* var. nov. with metal ions and chitin)
- $T_5$: Comparative treatment with commercial product (VYDATE, oxamyl)

The amount present of the fungus *Glomus iranicum* var. *tenuihypharum* var. nov. in the treatments in which the fungus was inoculated has been estimated. Between 1 and 5 grams of mycelium-spores of this species was produced in 1 kg of soil, which is a range between 0.1 and 0.5%. On the other hand, the root system in which it is produced, reached 10% of the gross weight (100 g). Fine rootlets, which are those mycorrhized, were 40 g per 1 kilogram of soil, i.e. 4% of the total weight. From these fine rootlets, only 75% has mycorrhizal propagules, therefore, the percentage of mycorrhizae in one kilogram of soil was equivalent to 3%.

The composition of the invention used in Treatment $T_3$ contains *Glomus iranicum* var. *tenuihypharum* var. nov.; the concentrations of chitin and metal ions in said composition were: chitin 5% by weight, 5% by weight Fe, Ca 4% by weight and Mg 1% by weight.

4 repetitions of each treatment were carried out for preventive treatment and similarly for curative treatment. Each experimental unit consists of 2 growing containers of 30 L volume, containing 2 plants each. Plants were selected randomly in each treatment, or plants that had suffered viruses, mishap or abnormality were selected. The rows and containers corresponding to the entire periphery of the assay were not part of it to avoid the edge effect.

Irrigation and fertilization was common throughout the test plot. Discharge was established at 4 l/h per growing container, divided into two discharge points for all treatments.

The irrigation water used for carrying out the assay came from the Tajo-Segura transfer system. The irrigation water was alkaline and slightly saline, with somewhat elevated levels of sodium and chloride ion, but in no way limiting for the crop object of the assay.

The inoculum used was taken from a batch of peat with tomato roots infested with phyto-parasitic nematodes from greenhouses from Mazarrón, province of Murcia. The inoculum was homogenized and multiplied to ensure adequate distribution of the nematode population and ensure sufficient population for the second inoculation.

In the previous analysis for the identification of phyto-parasitic nematodes, a high population of *Meloidogyne* was identified, followed by *Heterodera* and hardly any *Globodera* individual.

The first inoculation was made to coincide with the date of planting of the curative part of the assay. The second inoculation was made only in the preventive part of the assay, two days before the first application of the products. The growing cycle was 9 months.

Nematode inoculation of the curative assay was performed coinciding with the transplantation of the tomato. One month later, the nematode inoculation of the preventive assay was performed. Two days later it was performed the first application (inoculations of the composition of the invention and application of Vydate) and the second application (inoculations of the composition of the invention and application of Vydate) was performed 2 months later.

The balance of the elements N, P, K, Ca and Mg used during the growing cycle was: N, 12.8 mM; P, 1.4 mM; K, 5.5 mM Ca, 4.8 mM; Mg, 2.4 mM. Fertilizer concentrations provided to achieve this balance were: 72% phosphoric acid 0.117 cm³/l, calcium nitrate 0.379 g/l, potassium nitrate 0.547 g/l, ammonium nitrate 0.120 g/l, micronutrient mixture 0.020 g/l. The following parameters were used in the irrigation controller: final pH 5.5, in order to obtain pH 6 in the dropper, estimated consumption 59% nitric acid 0.07 l/m³, final electrical conductivity (EC) 2.1 dS/m, EC increase 0.8 dS/m.

The following table shows the phytosanitary treatments performed.

TABLE 8

Phytosanitary treatments

| Date | Active matter | Product | Dose | Mode of use | Cause |
|---|---|---|---|---|---|
| 06/10/11 | Pymetrozine 50% WG | Plenum | 50 g/Hl | 16L Backpack | Whitefly |
| 11/10/11 | Cyprodinil 37.5% + fludioxinil 25% | Switch | 100 g/hl | 16L Backpack | *Botrytis* |
| 11/10/11 | *Bacillus thuringiensis* 2.5% WG | Turex | 20 g/Hl | 16L Backpack | Worm |
| 16/11/11 | Pymetrozine 50% WG | Plenum | 50 g/Hl | 16L Backpack | Whitefly |
| 24/11/11 | Pymetrozine 50% WG | Plenum | 50 g/Hl | 16L Backpack | Whitefly |
| 09/11/11 | Pymetrozine 50% WG | Plenum | 50 g/Hl | 16L Backpack | Whitefly |
| 09/11/11 | *Bacillus thuringiensis* 2.5% WG | Turex | 20 g/Hl | 16L Backpack | Worm |
| 03/02/12 | Imidacloprid 20% SL | Confidor | 75 cc/Hl | 16L Backpack | Fly, Aphid |
| 15/02/12 | *Bacillus thuringiensis* 2.5% WG | Turex | 20 g/Hl | 16L Backpack | Worm |
| 07/03/12 | Methiocarb 50% WP | Mesurol | 100 g/Hl | 100 l Cask | Trip |
| 07/03/12 | *Bacillus thuringiensis* 2.5% WG | Turex | 20 g/Hl | 100 l Cask | Worm |
| 21/03/12 | Pyriproxyfen 10% EC | Brai | 75 cc/Hl | 100 l Cask | Fly, Aphid |
| 12/04/12 | Imidacloprid 20% SL | Confidor | 75 cc/Hl | 100 l Cask | Fly, Aphid |
| 12/04/12 | *Bacillus thuringiensis* 2.5% WG | Turex | 20 g/Hl | 100 l Cask | Worm |
| 02/05/12 | Flubendiamide 24% WG | Fenos | 25 g/Hl | 100 l Cask | Tuta, Moth |
| 09/05/12 | Flubendiamide 24% WG | Fenos | 25 g/Hl | 100 l Cask | Tuta, Moth |
| 17/05/12 | Spinosad 48% SC | Spintor | 25 cc/Hl | 100 l Cask | Tuta, Trip, Fly |
| 01/06/12 | Spinosad 48% SC | Spintor | 25 cc/Hl | 100 l Cask | Tuta, Trip, Fly |
| 01/06/12 | Cyprodinil 37.5% + fludioxinil 25% | Switch | 100 g/hl | 100 l Cask | *Botrytis* |
| 20/06/12 | Spinosad 48% SC | Spintor | 25 cc/Hl | 100 l Cask | Tuta, Trip, Fly |
| 20/06/12 | *Bacillus thuringiensis* 2.5% WG | Turex | 20 g/Hl | 100 l Cask | Worm |

Evaluation of Galling

For each treatment 2 extractions were performed at the beginning under curative to assess the infestation level and under preventive at the end of cultivation for the same purpose.

The first extraction was performed at 45 days after inoculation of nematodes and 7 days after application of the product to be tested. High resolution scanning was performed, enlarging live roots submerged in osmosis water, observing a high percentage of galls in all treatments, indicating a high population of nematodes.

The second extraction was performed at 120 days after inoculation and 83 days after application of the product to be tested. At this point, a significant difference between treatments was already clearly appreciated, the treatments with the composition of the invention having a smaller number of galls and a greater number of active rootlets.

A third extraction was carried out at the end of cultivation of plants belonging to the preventive portion to estimate the degree of infestation of nematodes in all treatments.

The same difference was observed in root architecture and development than at 120 days, the product to be tested showing better results, as it was shown in the scanning of living roots submerged in osmosis water.

Root Analysis 9 soil and 2 root extractions were carried out for each treatment to assess root thickness, root colonization, external mycelium, total microflora and nematology.

The following tables set out the total values of mycorrhizal colonization, extramatrical mycelium and nematology corresponding to data taken in the nine extractions made throughout the growing cycle.

Mycorrhizal Colonization

TABLE 9

Mycorrhizal colonization in curative treatment

| Days | Control (%) | *Glomus iranicum* var. *tenuihypharum* var. nov. (%) | Composition of the invention (%) | Vydate (%) |
|---|---|---|---|---|
| 0 d | 11 | 4 | 2 | 10 |
| 30 d | 15 | 19 | 10 | 2 |
| 60 d | 18 | 38 | 40 | 5 |
| 90 d | 16 | 56 | 57 | 4 |
| 120 d | 9 | 63 | 59 | 8 |
| 150 d | 15 | 65 | 63 | 9 |
| 180 d | 33 | 67 | 71 | 18 |
| 210 d | 20 | 69 | 82 | 18 |
| 240 d | 18 | 74 | 89 | 22 |

TABLE 10

Mycorrhizal colonization in preventive treatment

| Days | Control (%) | Glomus iranicum var. tenuihypharum var. nov. (%) | Composition of the invention (%) | Vydate (%) |
|---|---|---|---|---|
| 0 d | 13 | 2 | 5 | 12 |
| 30 d | 4 | 32 | 27 | 2 |
| 60 d | 10 | 36 | 39 | 8 |
| 90 d | 2 | 25 | 70 | 12 |
| 120 d | 22 | 66 | 70 | 22 |
| 150 d | 28 | 75 | 82 | 24 |
| 180 d | 22 | 78 | 82.3 | 16 |
| 210 d | 28 | 85 | 87 | 22 |
| 240 d | 24 | 71 | 89 | 24 |

Rootlets samples were taken, washed with deionized water and clarified with a 10% solution of KOH for 10 minutes at 90° C. Subsequently they were passed through 2N HCl for 10 minutes and finally they were stained with a 0.05 lacto glycerin—Trypan Blue solution.

As shown by the data, the treatment with the composition of the invention has been the one that has obtained greater mycorrhizal colonization reaching 89% both in the curative part and in the preventive part of the assay. Mycorrhizal values achieved in the treatment with *Glomus iranicum* var. *tenuihypharum* var. nov. were lower in the presence of metal ions and chitin. Both curative and preventive conditions affected the colonization of the native AMF, becoming more negative in the presence of Vydate, which undoubtedly affected native mycorrhization.

Extramatrical Mycelium

TABLE 11

Extramatrical mycelium in curative treatment

| Days | Control (mg/kg soil) | Glomus iranicum var. tenuihypharum var. nov. (mg/kg soil) | Composition of the invention (mg/kg soil) | Vydate (mg/kg soil) |
|---|---|---|---|---|
| 30 d | 223.5 | 260.1 | 248.3 | 173.8 |
| 60 d | 173.8 | 360.1 | 260.8 | 223.5 |
| 90 d | 273.2 | 434.6 | 422.2 | 161.4 |
| 120 d | 223.5 | 571.2 | 471.8 | 173.8 |
| 150 d | 347.7 | 347.7 | 682.9 | 173.8 |
| 180 d | 347.7 | 533.9 | 720.7 | 186.3 |
| 210 d | 173.8 | 260.8 | 397.3 | 235.0 |
| 240 d | 484.3 | 645.7 | 608.4 | 183.6 |

TABLE 12

Extramatrical mycelium in preventive treatment

| Days | Control (mg/kg soil) | Glomus iranicum var. tenuihypharum var. nov. (mg/kg soil) | Composition of the invention (mg/kg soil) | Vydate (mg/kg soil) |
|---|---|---|---|---|
| 30 d | 223.5 | 347.7 | 285.6 | 161.4 |
| 60 d | 260.8 | 360.1 | 335.3 | 186.3 |
| 90 d | 298.0 | 298.0 | 434.6 | 161.4 |
| 120 d | 322.8 | 397.3 | 409.8 | 161.4 |
| 150 d | 248.3 | 682.9 | 620.8 | 149.0 |
| 180 d | 447.0 | 397.3 | 645.7 | 223.5 |
| 210 d | 235.9 | 260.8 | 447.0 | 149.0 |
| 240 d | 422.7 | 471.8 | 831.9 | 322.8 |

Following centrifugation and decanting of a 50 g soil aliquot, all the material collected in the 40 micron sieve was taken, it was passed through a mixer at 900 rpm, it was vacuum filtered and the collected material was taken in 5 40 mg replicates, and it was evaluated under dissecting microscope. Two imaginary lines, horizontally and vertically, were counted and the average of mycelia counted was multiplied by the correction factor, 0.000745 and it was extrapolated to mg of mycelium per gram of sample.

The extramatrical mycelium evolution was similar to mycorrhizal colonization, as well as in the percentage of colonization the higher values were reported for the treatment with the composition of the invention. The mycelium values were higher in the presence of metal ions and chitin, however, plants treated only with *Glomus iranicum* var. *tenuihypharum* var. nov. also achieved high concentration of this parameter, in comparison with the control and treatment with Vydate, which further decreased the expression of the native fungi extramatrical mycelium. Like the colonization percentage, values were very similar for the two conditions of application, the curative treatment producing the greatest stimulation.

Nematode Counts in the Curative Treatment

TABLE 13

Live juvenile nematodes count

| Days | Control (n) | Glomus iranicum var. tenuihypharum var. nov. (n) | Composition of the invention (n) | Vydate (n) |
|---|---|---|---|---|
| 0 | 52.5 | 27 | 51.5 | 55 |
| 30 | 46.5 | 48 | 36.5 | 15.5 |
| 60 | 61 | 44 | 23 | 16.5 |
| 90 | 63 | 57.5 | 42 | 29.5 |
| 120 | 44.5 | 32.5 | 30.5 | 78.5 |
| 150 | 155.5 | 104.5 | 22.5 | 33 |
| 180 | 137 | 67 | 31 | 42.5 |
| 210 | 59 | 62.5 | 14 | 23 |
| 240 | 182 | 16.5 | 19.5 | 73.5 |

TABLE 14

Dead juvenile nematodes count

| Days | Control (n) | Glomus iranicum var. tenuihypharum var. nov. (n) | Composition of the invention (n) | Vydate (n) |
|---|---|---|---|---|
| 0 | 68.5 | 26.5 | 54 | 40 |
| 30 | 31.5 | 71.5 | 88.5 | 30.5 |
| 60 | 102 | 153 | 114 | 86.5 |
| 90 | 65 | 106 | 185 | 67.5 |
| 120 | 106.5 | 86.5 | 113 | 118 |

TABLE 14-continued

Dead juvenile nematodes count

| Days | Control (n) | Glomus iranicum var. tenuihypharum var. nov. (n) | Composition of the invention (n) | Vydate (n) |
|---|---|---|---|---|
| 150 | 66 | 251 | 127 | 49.5 |
| 180 | 82 | 143.5 | 158.5 | 33 |
| 210 | 20 | 27 | 41 | 5.5 |
| 240 | 34 | 6 | 54 | 38.5 |

TABLE 15

Mortality rate

| Days | Control (% m) | Glomus iranicum var. tenuihypharum var. nov. (% m) | Composition of the invention (% m) | Vydate (% m) |
|---|---|---|---|---|
| 0 | 56.8% | 63.0% | 51.4% | 42.1% |
| 30 | 40.4% | 59.9% | 70.7% | 66.5% |
| 60 | 62.6% | 77.7% | 83.2% | 84.2% |
| 90 | 50.8% | 64.9% | 81.8% | 69.2% |
| 120 | 70.5% | 72.4% | 79.8% | 53.9% |
| 150 | 29.8% | 72.0% | 84.8% | 60.0% |
| 180 | 39.6% | 68.2% | 83.7% | 43.8% |
| 210 | 25.3% | 32.1% | 73.9% | 19.1% |
| 240 | 16.0% | 27.0% | 73.4% | 34.7% |

The analysis of the evolution of the nematode population in soil was carried out from the juveniles count (J2) and the mortality rates of their populations. It was found that both Vydate treatment and the treatment with the composition of the invention, kept very similar J2 levels throughout the assay, showing the control by these treatments, but not for the case of the application of *Glomus iranicum* var. *tenuihypharum* var. nov. and absolute control.

However, it was found that the application of the composition of the invention promoted the highest mortality rates, also these were constant from day 60 until the end of the assay, which demonstrates its power as bio-nematicide, due to the effect promoted by the combined action on one part of the mycorrhizal fungi, and on the other part of metal ions and chitin which stimulated nematode destruction in the rhizosphere. The chemical control treatment reached the highest rates at 60 days, but its effectiveness was closely related to the punctual moments of its application and not sustained as with the previous case.

The *Glomus iranicum* var. *tenuihypharum* var. nov. strain alone had mortality values above 60%, and after 6 months, its activity declined significantly. Absolute control had the worst mortality rates in soil.

Nematode Counts in the Preventive Treatment

TABLE 16

Live juvenile nematodes count

| Days | Control (n) | Glomus iranicum var. tenuihypharum var. nov. (n) | Composition of the invention (n) | Vydate (n) |
|---|---|---|---|---|
| 0 | 70.5 | 130 | 53 | 53 |
| 30 | 91.5 | 43 | 45.5 | 14 |
| 60 | 41.5 | 15.5 | 4.5 | 3.5 |
| 90 | 143.5 | 58 | 38 | 49.5 |
| 120 | 52.5 | 33 | 32.5 | 7 |
| 150 | 45 | 168 | 62 | 41 |
| 180 | 162.5 | 173 | 108.5 | 37 |
| 210 | 63 | 63.5 | 14.5 | 30.5 |
| 240 | 82 | 71.5 | 14 | 65 |

TABLE 17

Dead juvenile nematodes count

| Days | Control (n) | Glomus iranicum var. tenuihypharum var. nov. (n) | Composition of the invention (n) | Vydate (n) |
|---|---|---|---|---|
| 0 | 119 | 221.5 | 99.5 | 116 |
| 30 | 21.5 | 56 | 99.5 | 30 |
| 60 | 184.5 | 103 | 45 | 29.5 |
| 90 | 95 | 130 | 212 | 105 |
| 120 | 109 | 146 | 125.5 | 47.5 |
| 150 | 108 | 201.5 | 177.5 | 140 |
| 180 | 107 | 197 | 179.5 | 50 |
| 210 | 17 | 24 | 44 | 43.5 |
| 240 | 17 | 18.5 | 63.5 | 54 |

TABLE 18

Mortality rate (%)

| Days | Control (n) | Glomus iranicum var. tenuihypharum var. nov. (n) | Composition of the invention (n) | Vydate (n) |
|---|---|---|---|---|
| 0 | 41.0% | 49.7% | 46.6% | 53.1% |
| 30 | 19.1% | 56.7% | 68.6% | 67.8% |
| 60 | 81.6% | 86.6% | 90.9% | 89.7% |
| 90 | 41.7% | 68.9% | 84.8% | 70.3% |
| 120 | 67.7% | 83.4% | 81.9% | 87.0% |
| 150 | 71.1% | 59.7% | 72.3% | 77.8% |
| 180 | 39.5% | 53.7% | 62.0% | 57.3% |
| 210 | 21.4% | 28.6% | 75.8% | 58.4% |
| 240 | 17.2% | 20.7% | 81.0% | 45.3% |

In the preventive case the Vydate treatment kept J2 levels lower than the treatment with the composition of the invention, however, in both cases it was possible to control the nematode population compared with the rest of the treatments that maintained very similar levels throughout the assay.

The analysis of the mortality rate in these conditions yielded results that were very similar to the curative case, so the application of the composition of the invention promoted the highest mortality rates and these were also constant from day 60 until the end of the assay. The chemical control treatment reached the highest rates at 60 and 120 days, but then progressively decreased. Also here its effectiveness was closely related to the moments of its application and it was not sustained.

Both in curative and preventive conditions, the composition of the invention has shown to have a high mortality rate of nematodes, which remains at around 70-80% throughout the growing cycle. Vydate treatment, however, lost effectiveness over days.

Rhizosphere Activity in the Curative Treatment

Serial dilutions of rhizosphere soil samples were prepared. Subsequently, the concentrations of rhizosphere bacteria and fungi present in the different treatments were quantified by determining the most probable number of microorganisms. For bacterial growth nutrient agar medium was used and for fungi growth, Rose Bengal and potato dextrose agar.

Figure 1:
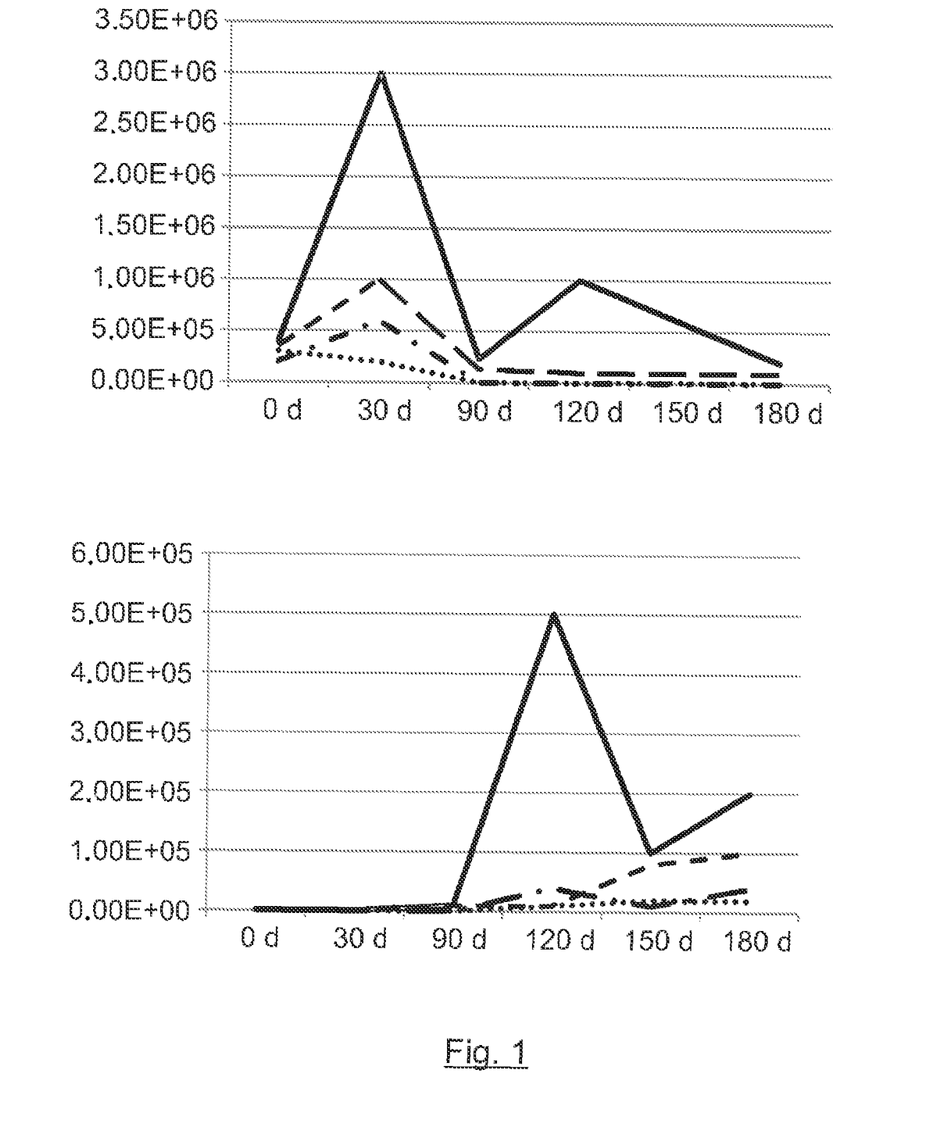
FIG. 1. It shows the results of total number of bacteria (cfu/ml soil, upper panel) or total number of fungi (cfu/ml soil, bottom panel) for different treatments under curative conditions. The results are depicted in the presence of *Glomus iranicum* var. *tenuihypharum* var. nov. (dashed line), in the presence of *Glomus iranicum* var. *tenuihypharum* var. nov. with metal ions and chitin (solid line), in the presence of the compound Vydate (dashed and dotted line) and control results (dotted line).

The graphs of the microbial evolution of the total microflora (bacteria and fungi) throughout the assay in the curative treatments (FIG. 1) illustrate the stimulatory effect associated with treatment of the composition of the invention on nematode control, the colonization itself, the mycorrhizal activity and also in stimulating the rhizosphere microorganisms. A slight stimulatory effect was also observed in the treatment with HMA alone, indicating that despite the known hyphosphere stimulation that occurs in arbuscular mycorrhizal associations, these are enhanced even more in the presence of metal ions and chitin.

Rhizosphere Activity in the Preventive Treatment

Figure 2:
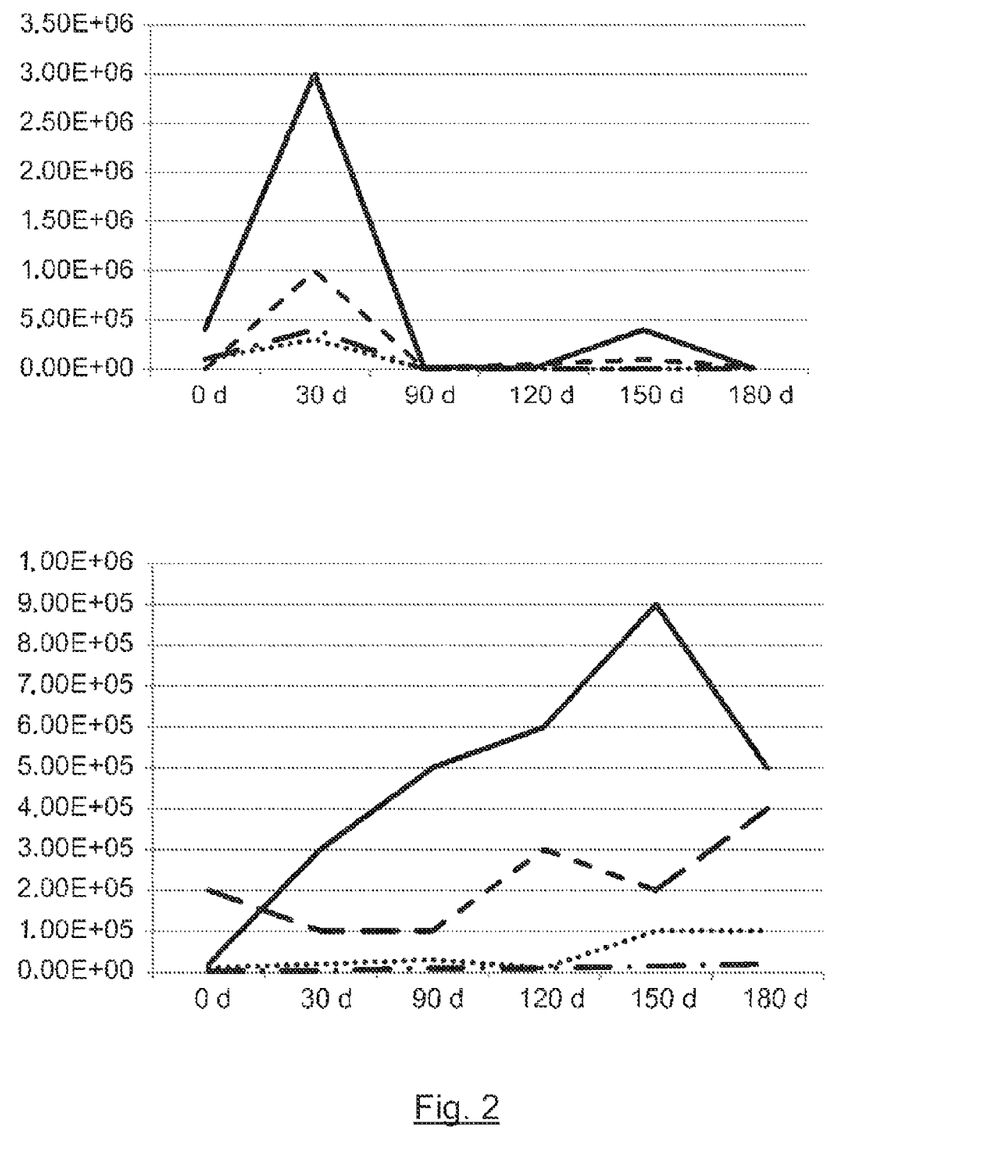
FIG. 2. It shows the results of total number of bacteria (cfu/ml soil, upper panel) or total number of fungi (cfu/ml soil, bottom panel) for different treatments under preventive conditions. The results are depicted in the presence of *Glomus iranicum* var. *tenuihypharum* var. nov. (dashed line), in the presence of *Glomus iranicum* var. *tenuihypharum* var. nov. with metal ions and chitin (solid line) in the presence of the compound Vydate dashed and dotted line) and control results (dotted line).

The results are shown in FIG. 2. In the treatments under preventive conditions the same effect found under the curative conditions was obtained.

It is good to note the low microbial activity found in the control treatment and in the Vydate treatment. This low activity is due to severe effects in control plants by nematode attack and a disinfectant effect of Vydate that caused a very significant decrease of microbial populations.

Production and Quality

Each treatment was harvested under curative and preventive conditions and the fruits were counted and weighed. The fruits affected with some defect or disease were discarded.

Only the fruits having some defect or disease were considered as rejections, and they are discarded. Small fruits were not discarded. Once the collection started, it was harvested about once a week until the end of the crop.

The total data of each of the varieties in the preventive and curative treatment are shown below:

TABLE 19

Daniela Tomato (curative treatment)

| | Weight (g) | Number of fruits | Average weight | Number of plants | Fruits/ plant | Weight (g/ plant) |
|---|---|---|---|---|---|---|
| Control | 27113.7 | 315 | 101.7 | 6 | 52.5 | 4519.0 |
| Glomus iranicum var. tenuihypharum var. nov. | 45453.4 | 388 | 115.2 | 5 | 77.6 | 9090.7 |
| Composition of the invention | 49444.2 | 390 | 124.1 | 4 | 97.5 | 12361.1 |
| Vydate | 46672.3 | 385 | 130.5 | 7 | 55.0 | 6667.5 |

TABLE 20

Daniela Tomato (preventive treatment)

| | Weight (g) | Number of fruits | Average weight | Number of plants | Fruits/ plant | Weight (g/ plant) |
|---|---|---|---|---|---|---|
| Control | 40625.8 | 380 | 118.5 | 6 | 63.3 | 6771.0 |
| Glomus iranicum var. tenuihypharum var. nov. | 55495 | 375 | 147.8 | 6 | 62.5 | 9249.2 |
| Composition of the invention | 64839.1 | 414 | 149.0 | 5 | 82.8 | 12967.8 |
| Vydate | 57619.9 | 452 | 134.4 | 6 | 75.3 | 9603.3 |

TABLE 21

Raf Tomato (curative treatment)

| | Weight (g) | Number of fruits | Average weight | Number of plants | Fruits/ plant | Weight (g/ plant) |
|---|---|---|---|---|---|---|
| Control | 23161.1 | 229 | 105.8 | 7 | 32.7 | 3308.7 |
| Glomus iranicum var. tenuihypharum var. nov. | 28997.4 | 241 | 115.6 | 6 | 40.2 | 4832.9 |
| Composition of the invention | 22626.6 | 235 | 96.7 | 5 | 47.0 | 4925.3 |
| Vydate | 23876 | 244 | 105.6 | 6 | 40.7 | 3979.3 |

TABLE 22

Raf Tomato (preventive treatment)

| | Weight (g) | Number of fruits | Average weight | Number of plants | Fruits/ plant | Weight (g/ plant) |
|---|---|---|---|---|---|---|
| Control | 27512.8 | 275 | 94.5 | 6 | 45.8 | 4585.5 |
| Glomus iranicum var. tenuihypharum var. nov. | 28334.3 | 234 | 127.5 | 6 | 39.0 | 4722.4 |
| Composition of the invention | 29132.4 | 243 | 114.2 | 6 | 40.5 | 4855.4 |
| Vydate | 24129.1 | 253 | 97.9 | 7 | 36.1 | 3447.0 |

Data of Brix degrees and hardness of the fruit were taken in alternate collections, five times in total throughout the production period in order to assess whether the quality of the fruit was affected in some way.

Total average data of each of the varieties in the preventive and curative treatment are shown below:

TABLE 23

Raf Tomato (hardness)

| RAF Hardness | T1 | T2 | T3 | T4 |
|---|---|---|---|---|
| Cur | 5.5 | 5 | 5 | 4.7 |
| Prev | 4.5 | 4.5 | 5.5 | 5.1 |

TABLE 24

Raf Tomato (° Brix)

| RAF ° Brix | T1 | T2 | T3 | T4 |
|---|---|---|---|---|
| Cur | 7.7 | 7.7 | 8.1 | 7.8 |
| Prev | 7.4 | 7.4 | 8.1 | 7.5 |

TABLE 25

Daniela Tomato (hardness)

| Daniela Hardness | T1 | T2 | T3 | T4 |
|---|---|---|---|---|
| Cur | 4.8 | 5.6 | 5 | 5.6 |
| Prev | 4.8 | 5.3 | 5.1 | 4.9 |

TABLE 26

Daniela Tomato (° Brix)

| Daniela ° Brix | T1 | T2 | T3 | T4 |
|---|---|---|---|---|
| Cur | 6.2 | 6.1 | 6.4 | 6 |
| Prev | 6.1 | 5.8 | 6.1 | 5.9 |

No drastic changes were appreciated in Brix degrees caused by the nematode population or by the applications of the products. The values were normal for both varieties reaching maximum Brix degrees midway through the cycle (8.1° Brix measured in the Raf variety and 6.4° Brix in the Daniela variety, both data belong to treatment T3).

The hardness of the fruit was not significantly affected since the penetrometer values are normal for each variety. In Raf the values are between 4.5 and 5.5 for all treatments and in Daniela 4.8 to 5.6. Therefore the fruits showed normal consistency both in the presence of the pest and after the application of the tested products.

The invention claimed is:

1. A method of treating a plant nematode infection comprising applying a composition comprising a strain of *Glomus iranicum* var. *tenuihypharum* var. nov. deposited under BCCM deposit number 54871 comprising the sequence identified by SEQ ID NO: 1, 2:1 smectite clays, metal ions and chitin to the plant in need thereof, wherein said composition is applied to the plant by means of seed treatment, root treatment, roots embedded in an emulsion, addition to irrigation water, irrigation, application of powder to the root system or application of emulsion injected into the root system.

2. The method according to claim 1, wherein said 2:1 smectite clays are dioctahedral or trioctahedral.

3. The method according to claim 1, wherein said 2:1 smectite clays are selected from the group consisting of sepiolite, attapulgite, nontronite and saponite.

4. The method according to claim 1, wherein a concentration of said *Glomus iranicum* var. *tenuihypharum* var. nov. strain is between 0.05 and 4% by weight.

5. The method according to claim 4, wherein said concentration is between 0.1 and 3% by weight.

6. The method according to claim 1, wherein the chitin concentration is between 2 and 10% by weight.

7. The method according to claim 1, wherein said metal ions are selected from the group consisting of Fe, Ca and Mg.

8. The method according to claim 1, wherein the composition further comprises Fe, Ca and Mg.

9. The method according to claim 7, wherein the concentration of Fe is between 3 and 12% by weight, the concentration of Ca is between 0.5 and 5% by weight and the concentration of Mg is between 0.2 and 2% by weight.

10. The method according to claim 1, wherein the form of presentation of said composition is powder, emulsifiable concentrate or granules.

11. The method according to claim 1, wherein said composition is a liquid, a solid or a gel.

12. The method according to claim 1, wherein the composition further comprises at least one fungicide, at least one bio-fungicide, at least one insecticide, at least one bio-insecticide, at least one nematicide and/or at least one bio-nematicide.

13. The method according to claim 12, wherein said fungicide is selected from the group consisting of Maneb, Mancozeb, Metalaxyl-Ridomil, Myclobutanil, Olpisan, Propamocarb, Quintozene, Streptomycin, Sulfur, Thiophanate-methyl, Thiram, triforine, Vinclozolin, Zinc white, Zineb, Ziram, Banrot, Fixed copper, Chlorothalonil, Chlorothalonil, Captan, Chloroneb, Cyproconazole, Zinc ethelene, bis-dithiocarbamate, Etridiazole, Fenaminosulf, Fenarimol, Flutolanil, Folpet, Fosetyl-AL and Iprodione.

14. The method according to claim 12, wherein said fungicide is selected from the group consisting of *Trichodermas* sp, *Bacillus subtilis, Bacillus licheniformis, Bacillus pumilus, Bacillus amyloliquefaciens, Streptomyces* sp, *Coniothyrium minitans* and *Pythium oligandrum*.

15. The method according to claim 12, wherein said insecticide is selected from the group consisting of organophosphate, carbamate and neonicotinoid.

16. The method according to claim 12, wherein said bio-insecticide is selected from the group consisting of *Bacillus* sp. *Chromobacterium* sp., *Beauveria* sp. and *Metarhizium* sp.

17. The method according to claim 12, wherein said nematicide is organophosphate or carbamate.

18. The method according to claim 12, wherein said bio-nematicide is *Pasteuria* sp.

19. Method for obtaining a composition according to claim 1, comprising:
   (a) coating inoculation of a seed of a host plant with the *Glomus iranicum* var. *tenuihypharum* var. nov. strain deposited under BCCM deposit number 54871,
   (b) cultivating said plant in watering cycles of between 7 to 10 days on a reproduction substrate comprising smectite clays in a percentage above 52% of the total weight of said substrate,
   (c) discontinuing said watering for a period equal to or greater than 20 days,
   (d) removing the aerial part of the plant and removing the substrate and
   (e) milling said substrate below 80 microns at a temperature between 25 and 30° C. to obtain said composition.

* * * * *